United States Patent [19]

Grigorian et al.

[11] Patent Number: 4,476,225

[45] Date of Patent: Oct. 9, 1984

[54] APPARATUS FOR CONTINUOUSLY DISINTEGRATING CELLS OF MICROORGANISMS

[75] Inventors: Alfred N. Grigorian; Andrei P. Kovalev, both of Moscow; Vitaly V. Lalov, Moskovskoi; Nikolai D. Makarov, Irkutsk; Rady V. Katrush, Moscow, all of U.S.S.R.

[73] Assignee: Vsesojuzny Nauchnoissledovatelsky Institut Sinteza Belkov, Moscow, U.S.S.R.

[21] Appl. No.: 397,122

[22] Filed: Jul. 12, 1982

[30] Foreign Application Priority Data

Nov. 13, 1981 [SU] U.S.S.R. ............... 3339317

[51] Int. Cl.³ .............. C12M 1/00; C12N 1/06; A47J 19/06; B02C 11/00
[52] U.S. Cl. ................... 435/287; 435/259; 241/2
[58] Field of Search ............ 435/287, 259, 812, 3, 435/289; 241/1, 2, 5, 301

[56] References Cited

U.S. PATENT DOCUMENTS 3,165,266 1/1965 Blum et al. ............... 435/287
4,084,757 4/1978 Rakitin et al. ............ 241/1

FOREIGN PATENT DOCUMENTS 492118 1/1973 U.S.S.R. .
602551 4/1978 U.S.S.R. .
602550 4/1978 U.S.S.R. .

OTHER PUBLICATIONS

Rees, "Evaluating Homogenizers for Chemical Processing", Chemical Engineering, May 13, 1974, pp. 87–92.

Primary Examiner—Raymond Jones
Assistant Examiner—Marianne S. Minnick
Attorney, Agent, or Firm—Fleit, Jacobson, Cohn & Price

[57] ABSTRACT

An apparatus for continuously disintegrating cells of microorganisms comprising a mixing vessel and an accumulating vessel communicating with one another through a disintegration device. The disintegration device comprises a hollow body having a seat in which there is installed a needle valve member. The hollow body further comprises a sleeve having a bottom wall incorporating the needle valve member and a side wall having openings for communicating the interior of the sleeve with the accumulating vessel. An insert is installed in the opened end of the sleeve which is connected to the sleeve and has a central passage coaxial with the valve member and communicating with the mixing vessel.

5 Claims, 3 Drawing Figures

APPARATUS FOR CONTINUOUSLY DISINTEGRATING CELLS OF MICROORGANISMS

FIELD OF THE ART

The invention relates to the microbiological industry, and more particularly, to an apparatus for continuously disintegrating cells of microorganisms such as yeast, bacteria, water plants and fungi for isolating intracellular proteins, nucleic acids, enzymes and other physiologically active substances.

BACKGROUND OF THE INVENTION

In isolating substances present in cells of microorganisms, e.g., in preparing concentrates of food-purpose protein, enzyme preparations and the like it is necessary to break down cell membranes. For that purpose, there are apparatus in which cell membranes are destructed by mechanical, chemical or fermentation methods.

Among the apparatus using the mechanical methods of disintegration of cells are known extrusion apparatus, ballistical disintegrators and apparatus using the effect of decompression, wherein the cells are destructed on the account of expansion of gas dissolved in the cells under pressure upon an abrupt pressure decrease in suspension. The invention relates to the latter type of apparatus.

Prior are apparatus for decompression disintegration consist of two basic units. The first unit comprises one or two high-pressure vessels having pipelines for feeding thereto a cell suspension and a working gas (nitrogen, air, carbon dioxide and the like) under pressure for saturating the suspension. The vessels can have a suspension level regulator and stirring devices. The second basic unit is a disintegration device which comprises a specially designed valve ensuring an abrupt pressure decrease in the flow of the cell suspension.

The prior art apparatus for decompression disintegration of cells of microorganisms differ from one another mainly in the construction of the disintegration device.

In one embodiment, the disintegration device comprises a construction consisting of a top flange casing and a bottom flange casing which are vertically movable and have disk seats installed therein, the disk seat of the bottom casing having an annular projection defining with the outer surface of the top seat a working aperture, and the top casing has a passage for admitting the suspension to the working aperture (cf. USSR Inventor's Certificate No. 602550, Int. Cl. C 12 K 1/10).

In another embodiment a similar construction of the disintegration device is used, which differs in that the seat of the bottom casing has an additional annular projection and a passage for the removal of the suspension of disintegrated cells, the disk seat of the top casing having a number of grooves communicating with the passage admitting the suspension for distributing the suspension into the working aperture; in addition, an agitator is provided on the top casing for cleaning the working aperture upon clogging (cf. USSR Inventor's Certificate No. 602551, Int. Cl. C 12 K 1/10).

The abovedescribed apparatus for decompression disintegration function in the following manner. A cell suspension and a compressed gas are continuously fed to a mixing vessel having a float-type level gauge. When the suspension level in the mixing vessel increases, the level gauge opens the admission of compressed gas thereto, the gas bubbling under pressure through the suspension layer. Further, the suspension saturated with the gas passes through a receiver and is admitted to the disintegration device.

In the disintegration device the suspension is fed to the disk seat of the top casing and is then throttled through the aperture defined between the outer surface of the top seat and the annular projection (or projections) of the bottom seat to pass to the zone of normal pressure. The cells are thus disintegrated under the action of a decompression. The working pressure in the disintegration device is set-up by tightening adjusting screws and is measured by means of a pressure gauge.

The apparatus for decompression disintegration are characterized by a high enough efficiency of breaking of the cell membranes with metal mass and energy consumption which are much lower than in apparatus of other types. The apparatus function at a comparatively low working pressure (between 80 and 200 atm.g.). The decompression method used in such apparatus makes it possible to scale-up such apparatus to the capacity required in the commercial production.

The abovedescribed apparatus are, however, deficient in a complicated construction of the disintegration device and the need in manual adjustment of pressure in the disintegration device during operation.

An apparatus for continuously disintegrating cells of microorganisms disclosed in USSR Inventor's Certificate No. 492118, Int. Cl. C 12 1/10 comprises a mixing vessel for allowing a suspension of microorganisms to stay under pressure, a pipeline of a disintegration device connected thereto and to an accumulating vessel for disintegrated material. Pipelines connected to a compressed gas source and to a metering pump for supplying the suspension are connected to the mixing vessel containing the suspension. The apparatus has an automatic valve for maintaining a pre-set pressure in the vessel.

The disintegration device comprises two casings connected in series to one another and defining a supply chamber and a working chamber. The supply chamber has an inlet passage for feeding the compressed gas and an outlet chamber for pressure decrease, and the working chamber has a lateral inlet passage for admitting the suspension of cells; the chambers are separated by a membrane to which is secured a valve member installed in the working chamber. The casing of the working chamber is connected in series with an adjusting flange body and a needle seat body, the needle bearing with its working end against the seat, so that the seat aperture is closed on the side of the high pressure zone.

The apparatus functions in the following manner. A working pressure in the supply chamber of the disintegration device is built-up by the compressed gas. Subsequently the suspension of cells is fed to the mixing vessel by the metering pump. When the pre-set working pressure (about 100 atm.g.) is achieved, the compressed gas is admitted to the vessel, and the suspension saturated with the gas is discharged through the distintegration device into the accumulating vessel.

In the initial position, when the compressed gas is admitted to the supply chamber of the disintegration device, the outlet from the working chamber is shut-off by the needle valve which bears against the needle seat. When the pressure in the working chamber becomes greater than that in the supply chamber as a result of operation of the metering pump, the membrane separating the chambers is caused to move upward together with the needle valve secured thereto, and an aperture is defined between the shut-off end of the needle and its seat so that the suspension is decompressed through this aperture into the accumulating vessel. This results in the cells being disintegrated owing to the decompression.

The uniformity of decompression of the cell suspension is ensured by means of the adjusting flange which is bolted to the casing of the working chamber of the disintegration device.

The apparatus functions continuously and enables the degree of disintegration of cells of microorganisms at a rate of 70-75%.

It should be, however, noted that the arrangement of the needle valve inside the working chamber and the lateral admission of the suspension to the working chamber in the abovedescribed apparatus result in swirling of the suspension flow in the passage defined between the working chamber walls and the needle and also in swirling of the suspension jet discharged through the aperture defined by the needle and its seat. As a result, the time of pressure decrease in the suspension increases thus lowering the efficiency of disintegration. In addition, the movement of the suspension jet at the outlet from the disintegration device determined by the shape of the aperture between the needle and its seat is directed toward the needle axis thus impairing the atomization of the suspension, hence, lowering the efficiency of disintegration.

The construction of the disintegration device consisting of four series-connected elements—the supply chamber, the working chamber, the adjusting flange and the needle seat—is difficult to adjust upon a change in the operating conditions and replacement of various components, thus making the apparatus as a whole more complicated in structure.

In extrusion disintegration apparatus the cells are disintegrated by throttling the cell suspension from a high-pressure zone through a microaperture of a disintegration valve into a normal pressure zone. One of the most popular apparatus of this type is a hydraulic extruder manufactured by the U.S. Company Gaulin (cf. Rees, L. H., Chem. Engineering, 1974, 5, 13, 87). The apparatus structurally consists of two basic units: a high-capacity plunger pump and a spring-biased cuneiform disintegrating valve which is connected to the pump discharge. Both units are installed on a cast iron bed, together with a motor. The hydraulic pressure at the disintegration valve is adjusted either manually, by means of a handwheel, or remotely. The apparatus is designed for operation under recirculation of the cell suspension.

In operation a suspension of microorganisms is continuously admitted at a high pressure (between 250 and 700 atm.g.) to the interior of the valve, at a low velocity. The suspension then gets into a microaperture between the valve and its seat where the velocity rapidly increases, depending on the working pressure, and the suspension is throttled into the normal pressure zone where the cells of microorganisms are disintegrated to the extent determined by the value of the hydrostatic pressure, its gradient and rate of change, cavitation and turbulization effects. The residence time of the cell suspension within the microaperture about 1 μm wide is $10^{-6}$ s.

The process of destruction of cells in the extrusion homogeneization apparatus features high working pressure (250-700 atm.g.), and the working cycle is to be repeated many a time for achieving high degree of cell disintegration (80-90%) so that fragments of cells of different size are obtained, and the separation of the solid and liquid phases of the resultant suspension becomes very difficult.

OBJECTS AND SUMMARY OF THE INVENTION

It is an object of the invention to provide an apparatus for continuously disintegrating cells of microorganisms in which the disintegration device is of a simple construction and features a simple adjustment capability while contributing to an improvement of the degree of disintegration of cells of microorganisms thus facilitating operation of the apparatus and making it more efficient.

With this and other objects in view, in an apparatus for continuously disintegrating cells of microorganisms, comprising a mixing vessel for saturating cells of microorganisms in suspension with a gas under pressure, having a metering pump and pipelines for admitting a suspension and a compressed gas, respectively, and an accumulating vessel for disintegrated material which communicates with the mixing vessel through a disintegrating device comprising a hollow body having a seat in which is installed a needle valve member, according to the invention, the hollow body comprises a sleeve having a bottom wall incorporating the needle valve member and a side wall having openings for communication of the interior of the sleeve with the accumulating vessel, an insert being installed in the open end of the sleeve which is connected to the sleeve and has a central passage coaxial with the valve member and communicating with the mixing vessel, the seat in the form of a throttle washer being installed in the central passage.

This construction of the disintegration device makes it possible to direct the flow of suspension passing through the aperture between the needle valve member and the throttle washer in the form of a radially fanning flow to a low-pressure zone without swirling of the flow since the shut-off end of the valve member faces the orifice of the throttle washer on the low-pressure zone side. All this contributes to a high degree of disintegration of cells in suspension.

According to the invention, the needle valve member is adjustably mounted in the bottom wall of the sleeve so as to set-up a desired size of the aperture between the needle valve member and the throttle washer when the operating conditions of the apparatus in terms of pressure and/or flow rate of suspension passing through the aperture are to be changed.

The insert is preferably connected to the sleeve by means of a threaded joint. This facility provides for an additional adjustment of the aperture between the needle valve member and throttle washer and also facilitates assembly and disassembly of the disintegration device for replacement of the worn needle valve member.

According to the invention, it is preferred to make the central passage of the insert diverging on the side of its entry in the throttle washer so as to provide for a free, unobstructed emergence of the suspension from the aperture between the needle valve member and throttle washer into the accumulating vessel thereby creating a higher pressure gradient in the process of disintegration and increasing the quantity of cells destructed in the disintegrator.

The throttle washer is preferably secured in the insert by means of a bushing and a flange which is fixed to the insert so as to ensure the alignment of the throttle washer in the insert and a rapid replacement of the throttle washer when it is worn or when the operating conditions of the disintegration device are to be changed.

BRIEF DESCRIPTION OF THE DRAWINGS

The invention will now be described with reference to a specific embodiment of an apparatus for continuously disintegrating cells of microorganisms constructed in accordance with the invention, illustrated in the accompanying drawings, in which:

FIG. 3 is an embodiment of a needle valve member.

DETAILED DESCRIPTION OF THE PREFERRED EMBODIMENT

Figure 1:
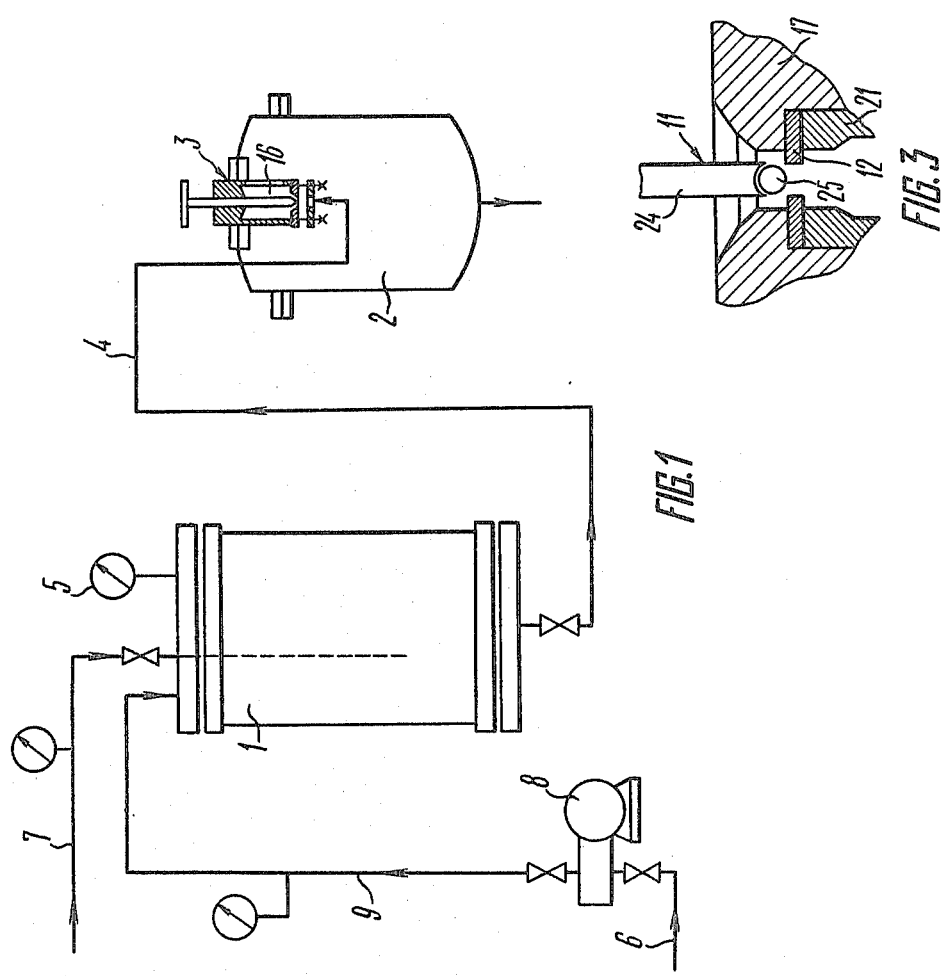
FIG. 1 is schematic view of an apparatus, according to the invention.

An apparatus for continuously disintegrating cells of microorganisms comprises a mixing vessel 1 (FIG. 1) for saturating a suspension of cells of microorganisms with a gas under pressure, an accumulating vessel 2 for disintegrated material, a disintegration device 3, a pipeline 4 for communication of the mixing vessel 1 with the disintegration device 3. The mixing vessel 1 is provided with a level sensor for monitoring the level of suspension in the vessel (not shown in FIG. 1), a pressure gauge 5 for measuring the pressure, pipelines 6 and 7 for admitting a suspension and a compressed gas, respectively, and a metering pump 8 communicating with the mixing vessel 1 through a pipeline 9.

If necessary, the mixing vessel 1 may have baffles, stirrers, a heat exchanger for thermostabilization (not shown in the drawings) and other means known per se for enabling normal operation of the apparatus.

The disintegration device 3 is accommodated within the accumulating vessel 2 so that the mixing vessel 1 communicates with the accumulating vessel 2 through the disintegration device 3.

The disintegration device 3 comprises a hollow body in the form of a sleeve 10, a needle valve member 11 in the form of a needle, and a seat in the form of a throttle washer 12, the pointed end of the valve member 11 being received in the orifice of the throttle washer. The other end of the needle valve member 11 is located in a low-pressure zone and is installed in a bottom wall 13 of the sleeve 10. A side wall 14 of the sleeve 10 has openings 15 for communicating the interior 16 of the sleeve 10 (FIG. 1) with the accumulating vessel 2. An insert 17 which is installed in the open end of the sleeve 10 (FIG. 2) is connected to the sleeve 10 and has a central passage 18 which is coaxial with the needle valve member 11 and communicates with the mixing vessel 1 through the pipeline 3 and with the accumulating vessel 2 through the interior 16, the throttle washer 12 being installed in the central passage 18.

The insert 17 is connected to the sleeve 10 by means of a threaded joint so as to provide for an adjustment of the position of the insert 17, together with the throttle washer 12, with respect to the valve member 11.

Figure 2:
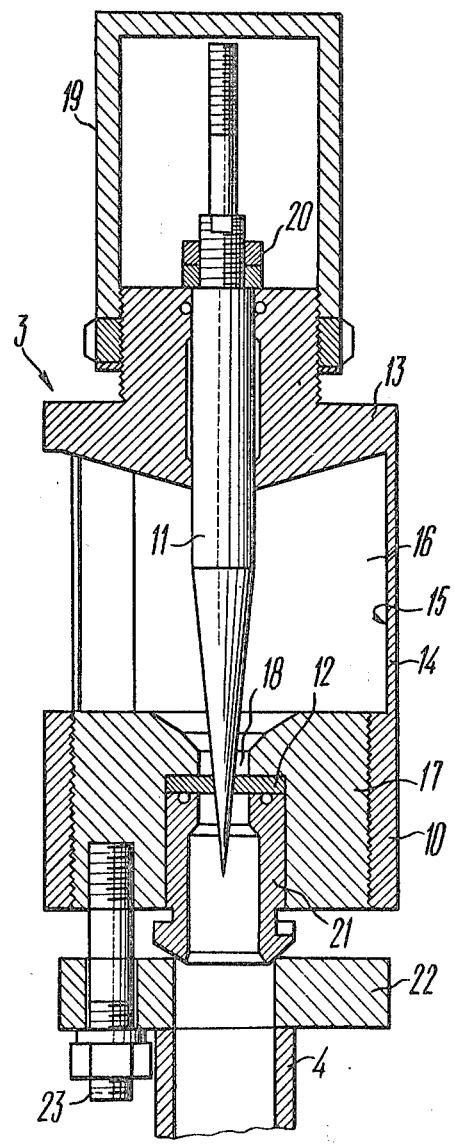
FIG. 2 is a longitudinal sectional view of a disintegration device of the apparatus shown in FIG. 1.

The central passage 18 of the insert 17 is made diverging on the side where the needle valve member 11 enters the throttle washer 12, as shown in FIG. 2.

The needle valve member 11 is installed with the possibility of adjustment in the bottom wall 13 of the sleeve 10, e.g., by means of a threaded joint defined by the bottom wall 13 of the sleeve 10 and a union nut 19 against which bears a shank of the valve member 11 which has a shoulder 20 limiting the vertical displacement of the valve member 11. By turning the union nut 19, the valve member 11 can be moved to adjust its position with respect to the seat, i.e. the washer 12 without disassembling the device.

The throttle washer 12 is secured in the insert 17 by means of a bushing 21 which is installed in the passage 18 of the insert and which is held in this position by a flange 22 of the pipeline 4, the flange 22 being fixed to the insert 17 by means of locking studs 23.

The needle valve member 11 may be in the form of a needle as shown in FIG. 2 or in the form of a rod 24 and a ball 25 as shown in FIG. 3.

The apparatus functions in the following manner.

With the orifice of the throttle washer 12 of the disintegration device 3 is completely shut-off by the needle valve member 11, a suspension of cells of microorganisms is fed to the mixing vessel 1 (FIG. 1) by means of the metering pump 8 through the pipelines 6 and 9; a compressed gas (nitrogen, air, carbon dioxide and the like) is also fed to the mixing vessel so as to bubble it through the suspension layer and to saturate the cells of microorganisms with the gas under pressure. The level of suspension in the mixing vessel 1 is pre-set and then maintained constant by means of a level sensor and a level regulator (not shown in the drawings) so that the ratio of the space occupied by the gas to the volume of suspension should be between 1:3 and 3:4. The working pressure is between 80 and 200 atm.g.

When the pre-set level of liquid in the mixing vessel 1 is achieved, the valve member 11 (FIG. 2) of the disintegration device 3 is moved vertically to open the orifice of the throttle washer 12. The reciprocations of the valve member 11 may be effected either manually or automatically, by means of an actuator. The suspension of microorganisms saturated with the gas starts flowing from the mixing vessel 1 through the pipeline 4 to the aperture defined between the valve member 11 and the throttle washer 12. The suspension pressure decreases at a high rate in the resultant aperture to the atmospheric pressure in the accumulating vessel 2 thus causing disintegration of cells of microorganisms owing the effect of decompression.

The apparatus then functions continuously to reliably ensure disintegration of cells at a rate of 75–80% within predetermined ranges of suspension velocity and flow rate.

Therefore, the employment of the apparatus according to the invention ensures an improvement of the disintegration efficiency by 5–8% owing to improved conditions for the discharge of the cell suspension jet through the throttling aperture of the disintegration device. At the same time, the simplification of the apparatus construction compared with the prior art makes it possible to facilitate the adjustment of the disintegration device, replacement of the valve member and throttle washer as they become worn and to automate the disintegration process.

We claim:

1. An apparatus for continuously disintegrating cells of microorganisms, comprising:

a mixing vessel for saturating cells of microorganisms in suspension with a gas under pressure;

a metering pump for suppling said cells of microorganisms in suspension to said mixing vessel;

a pipeline for feeding said cells in suspension to said mixing vessel, said pipeline connected at one end thereof to said metering pump and at the other end to said mixing vessel;

a pipeline for feeding a compressed gas to said mixing vessel;

a pipeline for communicating said mixing vessel to a disintegrating device;

an accumulating vessel for disintegrated material;

a disintegration device provided inside said accumulating vessel for communicating said accumulating vessel with said mixing vessel;

a hollow body of said disintegration device which is made in the form of a sleeve having a bottom wall, side walls and an open end;

openings in the side walls of the sleeve, the interior of the sleeve communicating with the accumulating vessel through said openings;

an insert provided in the open end of the sleeve and connected to the sleeve;

a central passage of said insert communicating with said mixing vessel and with the interior of the sleeve;

a seat in said central passage of said insert, said seat comprising a throttle washer situated to receive the pointed end of a needle valve member; and a needle valve member having its pointed end received in said throttle washer, the other end of the needle valve member being installed in the bottom wall of the sleeve.

2. An apparatus according to claim 1, wherein said needle valve member is adjustably mounted in the bottom wall of the sleeve.

3. An apparatus according to claim 1, wherein said insert is connected to the sleeve by means of a threaded joint.

4. An apparatus according to claim 1, wherein said central passage of the insert is made diverging on the side where the needle valve member enters said throttle washer.

5. An apparatus according to claim 1, wherein there is provided a bushing and a flange; said throttle washer being secured in said insert by means said bushing and said flange.

* * * * *